United States Patent
Desai et al.

(10) Patent No.: US 11,129,384 B2
(45) Date of Patent: Sep. 28, 2021

(54) POLYMORPHS OF MESOTRIONE METAL CHELATE AND PREPARATION PROCESS

(71) Applicant: UPL LTD, Haldia (IN)

(72) Inventors: Jignesh Amrutlal Desai, Mumbai (IN); Digish Manubhai Panchal, Mumbai (IN); Jaidev Rajnikant Shroff, Dubai (AE); Vikram Rajnikant Shroff, Dubai (AE)

(73) Assignee: UPL LTD, West Bengal (IN)

( * ) Notice: Subject to any disclaimer, the term of this patent is extended or adjusted under 35 U.S.C. 154(b) by 0 days.

(21) Appl. No.: 16/624,464

(22) PCT Filed: Jun. 15, 2018

(86) PCT No.: PCT/IB2018/054407
§ 371 (c)(1),
(2) Date: Dec. 19, 2019

(87) PCT Pub. No.: WO2018/234957
PCT Pub. Date: Dec. 27, 2018

(65) Prior Publication Data
US 2020/0113180 A1  Apr. 16, 2020

(30) Foreign Application Priority Data
Jun. 19, 2017 (IN) .............................. 201731021418

(51) Int. Cl.
| | | |
|---|---|---|
| *A01N 41/10* | (2006.01) | |
| *A01N 25/04* | (2006.01) | |
| *A01N 37/22* | (2006.01) | |
| *A01N 59/20* | (2006.01) | |
| *A01N 25/32* | (2006.01) | |
| *A01N 43/70* | (2006.01) | |

(Continued)

(52) U.S. Cl.
CPC ............. *A01N 41/10* (2013.01); *A01N 25/04* (2013.01); *A01N 37/22* (2013.01); *A01N 59/20* (2013.01); *A01N 25/32* (2013.01); *A01N 43/70* (2013.01)

(58) Field of Classification Search
CPC ........ A01N 41/10; A01N 25/04; A01N 37/22; A01N 59/20; A01N 25/32; A01N 43/70; A01N 43/84; C07B 2200/13; C07C 2601/14; C07C 317/24
See application file for complete search history.

(56) References Cited

U.S. PATENT DOCUMENTS 5,912,207 A   6/1999   Scher et al.

FOREIGN PATENT DOCUMENTS

| WO | 199727748 A1 | 8/1997 |
|---|---|---|
| WO | 2005055714 A2 | 6/2005 |
| WO | 2005060492 A1 | 7/2005 |

(Continued)

OTHER PUBLICATIONS

International Search Report and Written Opinion; International Application No. PCT/IB2018/054407; International Filing Date Jun. 15, 2018; dated Sep. 3, 2018; 18 pages.

*Primary Examiner* — Trevor Love
(74) *Attorney, Agent, or Firm* — Cantor Colburn LLP

(57) ABSTRACT

The invention provides mesotrione copper chelate form I and mesotrione copper chelate form II. A process for preparing mesotrione copper chelate form I and mesotrione copper chelate form II is also disclosed. Further, the present invention provides process for preparing mesotrione metal chelate polymorphs and agrochemical formulations comprising such polymorphs.

12 Claims, 4 Drawing Sheets

(51) Int. Cl.
*A01N 43/84* (2006.01)
*C07C 317/24* (2006.01)

(56) References Cited

FOREIGN PATENT DOCUMENTS

| WO | 2006021743 A1 | 3/2006 |
|----|---------------|--------|
| WO | 2007083242 A1 | 7/2007 |
| WO | 2011016018 A1 | 2/2011 |

US 11,129,384 B2

POLYMORPHS OF MESOTRIONE METAL CHELATE AND PREPARATION PROCESS

CROSS REFERENCE TO RELATED APPLICATIONS

This application is a National Stage application of PCT/IB2018/054407, filed on Jun. 15, 2018, which claims the benefit of Indian Application No. 201731021418, filed on Jun. 19, 2017, both of which are incorporated by reference in their entirety herein.

TECHNICAL FIELD OF THE INVENTION

The present invention relates to polymorphs of mesotrione metal chelate. The invention provides mesotrione metal chelate polymorphic forms and process for preparing the polymorphs. The invention further provides agrochemical formulations comprising such polymorphs.

BACKGROUND OF THE INVENTION

Cyclohexane-dione compounds exhibit herbicidal activity. Mesotrione is a cyclohexane-1,3-dione herbicide being developed for the selective control of a wide range of weeds in maize. The term 'mesotrione' herein means 2-(2'-nitro-4'-methylsulfonyl benzoyl)-1,3-cyclohexanedione including any enolic or tautomeric forms of the molecule. Further it includes all tautomeric, racemic and optical isomers derived from salts and various substituted mesotrione. Further it includes all agriculturally acceptable salts derived from mesotrione.

Mesotrione is a synthetic analog of a naturally occurring herbicidal product derived from the bottlebrush plant (*Callistemon citrines*). Mesotrione acts as p-Hydroxyphenyl pyruvate dioxygenase inhibitor, which ultimately affects carotenoid biosynthesis. Selectivity in maize derives from differential metabolism (to the 4-hydroxy derivative) and also possibly from slower foliar uptake. It is used for both pre-emergence and post-emergence control of broad-leaved weeds, such as *Xanthium strumarium, Ambrosia trifida, Abutilon theophrasti*, and *Chenopodium, Amaranthus* and *Polygonum* spp., and some grass weeds in maize.

Mesotrione is rapidly taken up by weed species following foliar application, and is distributed within the plants by both acropetal and basipetal movement. Maize is tolerant to mesotrione as a consequence of selective metabolism by the crop plant. Slower uptake of mesotrione, relative to susceptible weed species, may also contribute to its utility as a selective herbicide for use in maize.

It has been observed that water based formulations of active ingredients like mesotrione which are insoluble or partially soluble in water can suffer from a variety of problems such as chemical degradation, crystal formation, agglomeratrion, thickening or gel formation, serum formation, sedimentation, precipitation and the like. Such problem aggravates when the active ingredient has the ability to remain in different crystal forms or polymorphs.

Mesotrione exhibits polymorphism. U.S. Pat. Nos. 8,063,253 and 8,980,796 disclose different polymorphs of mesotrione and processes for preparing different polymorphs.

U.S. Pat. No. 8,063,253 discloses that form I polymorph of mesotrione is thermodynamically stable form and form II is the metastable form. The metastable form would gradually get convert to the thermodynamically stable form I. The formulation containing these forms can lead to stability issues during storage as well as during application of the formulation in the field.

U.S. Pat. No. 8,980,796 discloses polymorph-form 3 of mesotrione having improved physical and biological properties.

U.S. Pat. No. 5,912,207 discloses that herbicidal cyclohexane-dione compounds for instance, mesotrione have the disadvantage that in water and in certain solvents, they undergo degradation. Metal chelates has been prepared to overcome the problems associated with the degradation of mesotrione in aqueous formulations as well as in certain solvent conditions.

The interconversion of polymorphs, the drastic difference in their physical properties and their unpredictable properties in water and other solvents make it difficult to formulate mesotrione having desired physical and biological properties.

Inventors' attempt to develop formulations of mesotrione chelate in combination with other active ingredients led to stability problems and handling issues like sedimentation, thickening and precipitation. The observed problems are due to the larger particle size of mesotrione chelate. It require additional efforts to obtain the active ingredient having required uniform particle size and during such processes, morphological changes can occur to the particles which consequently lead to issues in formulations.

Another common concern for agrochemical formulation is with respect to the toxicological profile of the product. In certain cases products are not acceptable due to the possibility of eye irritation that can be caused while handling the formulation. This property may lead to restrictive labelling of the formulation product that limits the usefulness of the product for the intended use.

EPA signal word for marketed product for combination of mesotrione and S-metolachlor (Tradename: Camix) is 'Warning'. Formulations with such classification can impart an undesirable degree of eye irritancy to the formulation.

Therefore it is challenging to develop methods to improve existing formulation products of mesotrione devoid of the disadvantages of existing formulations.

OBJECTS OF THE INVENTION

It is an object of the present invention to provide mesotrione chelate polymorphs.

It is another object of the present invention to provide process for preparing mesotrione chelate polymorphs.

Another object of the present invention is to provide stable herbicidal formulations comprising mesotrione chelate polymorphs.

It is yet another object of the present invention to provide stable herbicidal formulation comprising mesotrione chelate polymorphs having an improved toxicological profile.

It is an object of the present invention to provide mesotrione copper chelate polymorphs.

SUMMARY OF THE INVENTION

The present invention provides mesotrione copper chelate form I.

The present invention provides mesotrione copper chelate form II.

The present invention further provides process for preparing mesotrione metal chelate polymorphs.

Additionally, the invention provides herbicidal formulation comprising mesotrione metal chelate polymorphs.

Further, the invention provides herbicidal formulation comprising mesotrione metal chelate polymorphs wherein the formulation is less eye irritant.

The invention additionally relates to a method of controlling undesired weed species said method comprising applying an effective amount of composition comprising mesotrione metal chelate polymorphs to weeds or to their locus.

DETAILED DESCRIPTION

The inventors of the present invention surprisingly found out that mesotrione chelate exists in different polymorphic forms. These crystalline forms exhibit distinct features as characterised by an X-ray powder diffractogram as well as other physical properties. It has been further found that by suitable processes two polymorphs of mesotrione metal chelate can be prepared which are suitable for making stable formulations. These novel polymorphs as well as preparation processes are described below.

Unexpectedly, the inventors of the present invention found out that different processes for preparing mesotrione metal chelate lead to different polymorphic forms of mesotrione metal chelate.

Further, the inventors of the present invention surprisingly noted that the formulations comprising a polymorphic form of mesotrione metal chelate lead to less eye irritancy.

The two innovative polymorphic forms of the present invention are referred to as mesotrione copper chelate form I and mesotrione copper chelate form II.

The invention further provides a process for preparing mesotrione metal chelate polymorphs.

Further there is provided processes for preparing mesotrione copper chelate form I and mesotrione copper chelate form II.

Most unexpectedly, inventors of the present invention found out that mesotrione copper chelate form I is suitable for preparing herbicidal compositions especially liquid compositions.

Accordingly there is provided herbicidal compositions comprising mesotrione copper chelate form I or mesotrione copper chelate form II.

Accordingly there is provided mesotrione copper chelate form I.

In an embodiment of the present invention, there is provided mesotrione copper chelate form I which exhibits a characteristic X-ray powder diffraction pattern.

In another embodiment, there is provided mesotrione copper chelate form I which exhibits an X-ray diffraction pattern expressed in 2θ(±0.2°), showing at least three of the following reflexes: 9.1, 10.6, 11.8, 13.7, 15.9, 16.6, 18.3, 21.4, 22.1, 22.4, 24.1 and 27.7.

In another embodiment of the present invention there is provided mesotrione copper chelate form I which exhibits an X-ray diffraction pattern expressed in) 2θ(±0.2°), showing at least five of the following reflexes: 9.1, 10.6, 11.8, 13.7, 15.9, 16.6, 18.3, 21.4, 22.1, 22.4, 24.1 and 27.7.

In yet another embodiment of the present invention there is provided mesotrione copper chelate form I which exhibits an X-ray diffraction pattern expressed in) 2θ(±0.2°), showing all of the following reflexes: 9.1, 10.6, 11.8, 13.7, 15.9, 16.6, 18.3, 21.4, 22.1, 22.4, 24.1 and 27.7.

In another embodiment, there is provided mesotrione copper chelate form I characterized by all of the following reflexes and interplanar spacings d as depicted in below table:

| Angle (2θ ± 0.2°) | Interplanar spacings(d) Å |
|---|---|
| 9.1 | 9.7 |
| 10.6 | 8.4 |
| 11.8 | 7.5 |
| 13.7 | 6.5 |
| 15.9 | 5.6 |
| 16.6 | 5.3 |
| 18.3 | 4.8 |
| 21.4 | 4.2 |
| 22.1 | 4.0 |
| 22.4 | 4.0 |
| 24.1 | 3.7 |
| 27.7 | 3.2 |

Figure 1:
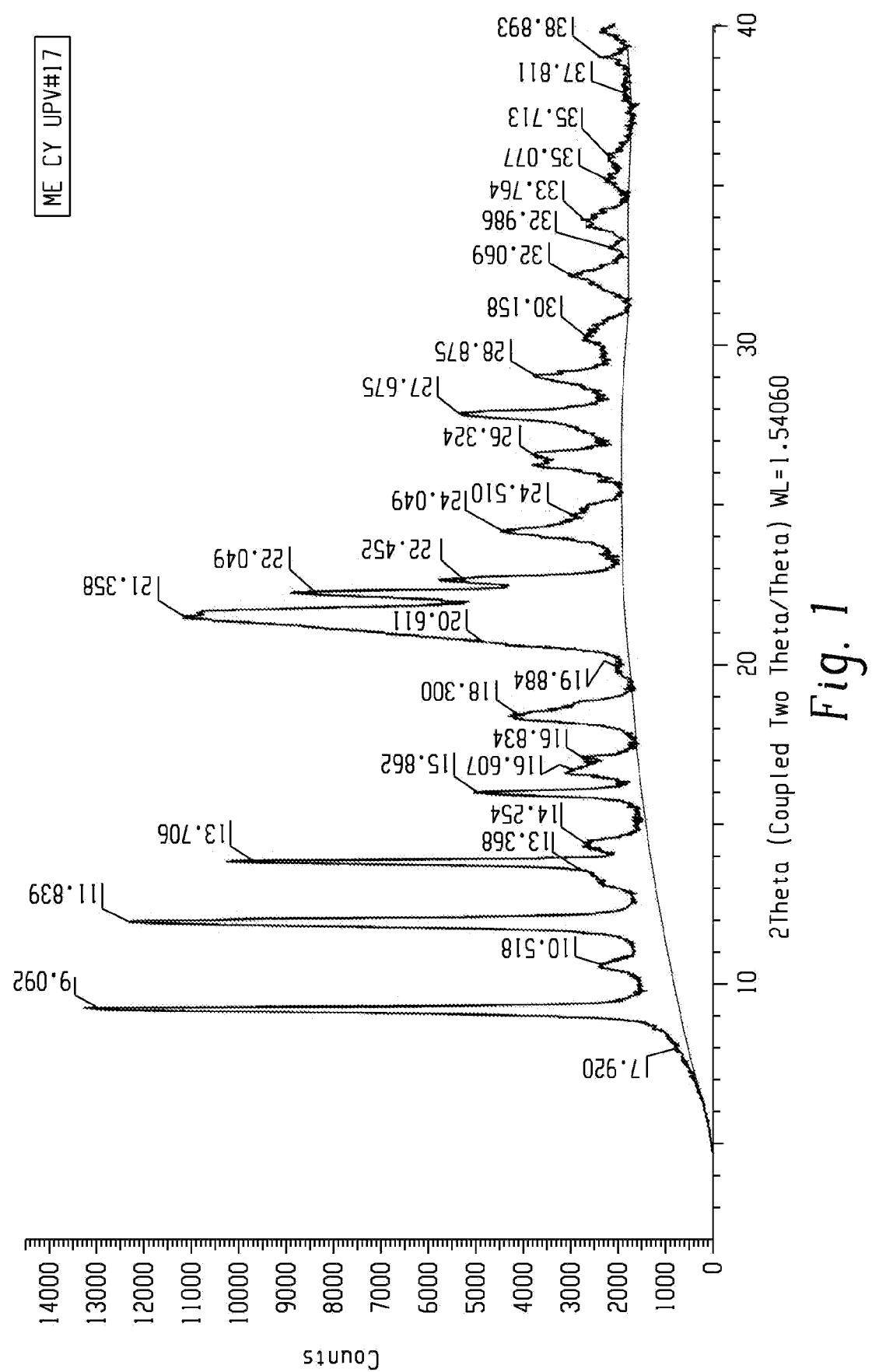
FIG. 1 shows a typical X-ray powder diffraction pattern of mesotrione copper chelate form I according to the present invention.
Figure 2:
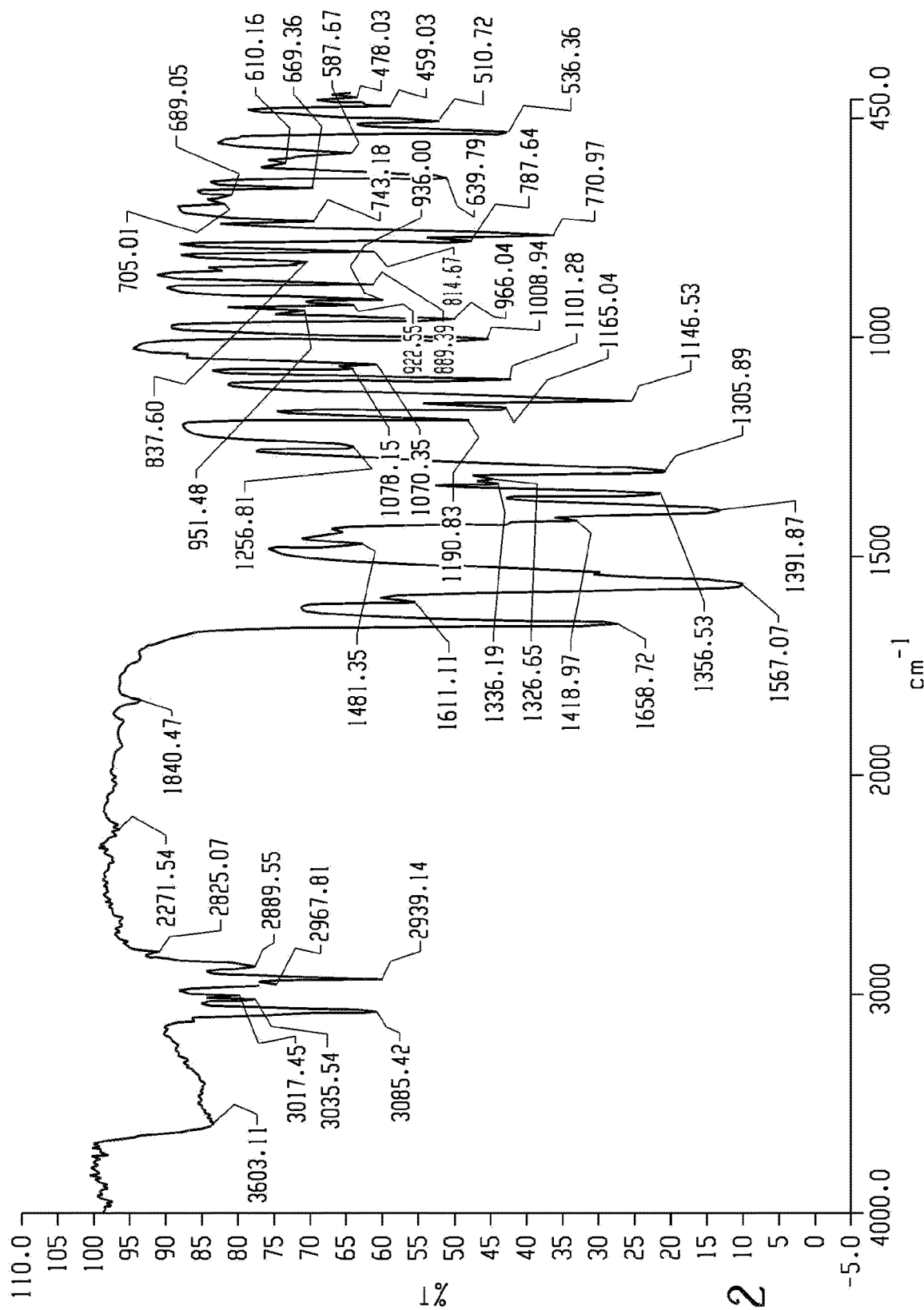
FIG. 2 shows a typical FT-IR spectrum of mesotrione copper chelate form I according to the present invention.
Figure 3:
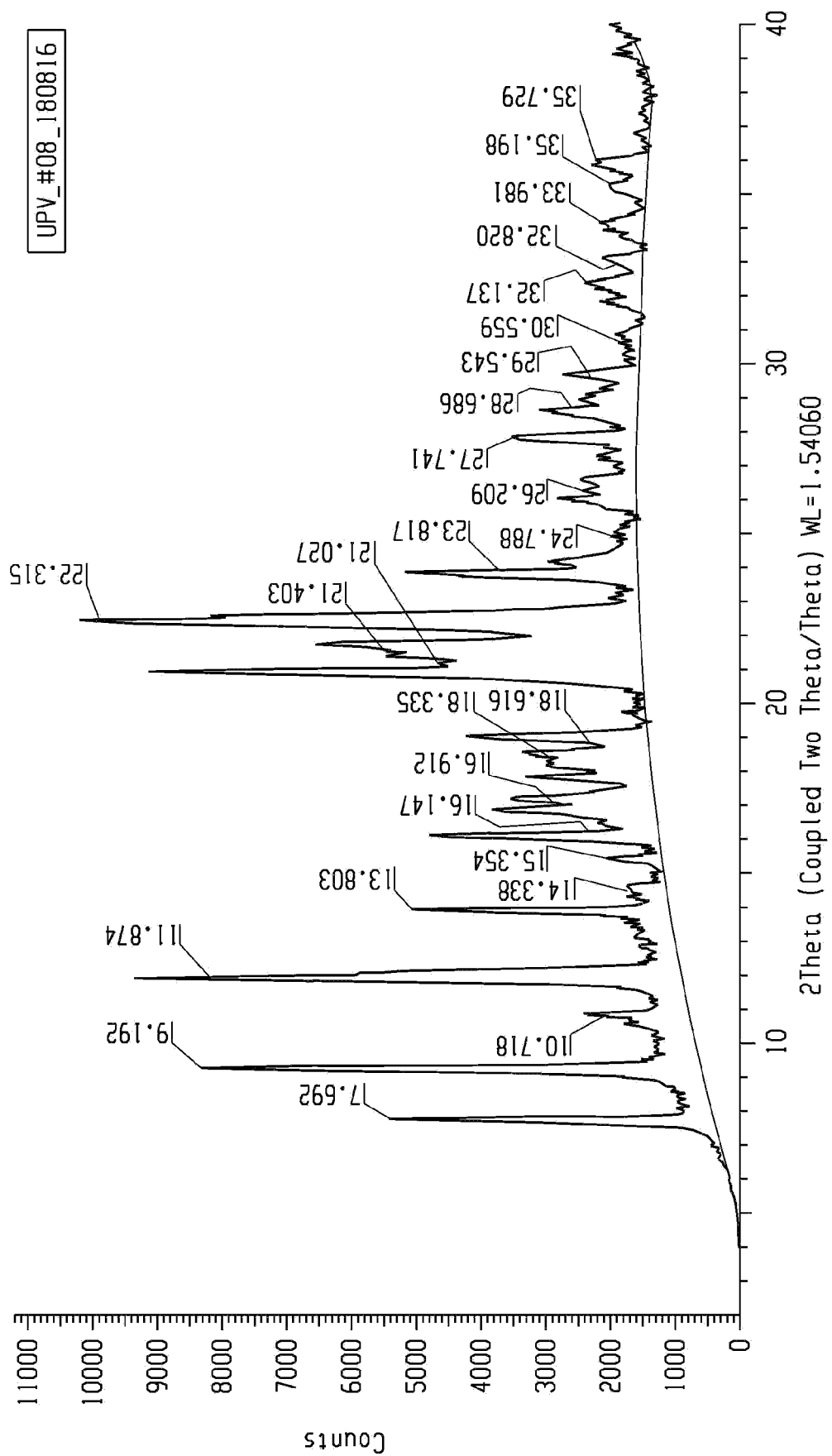
FIG. 3 shows a typical X-ray powder diffraction pattern of mesotrione copper chelate form II according to the present invention.
Figure 4:
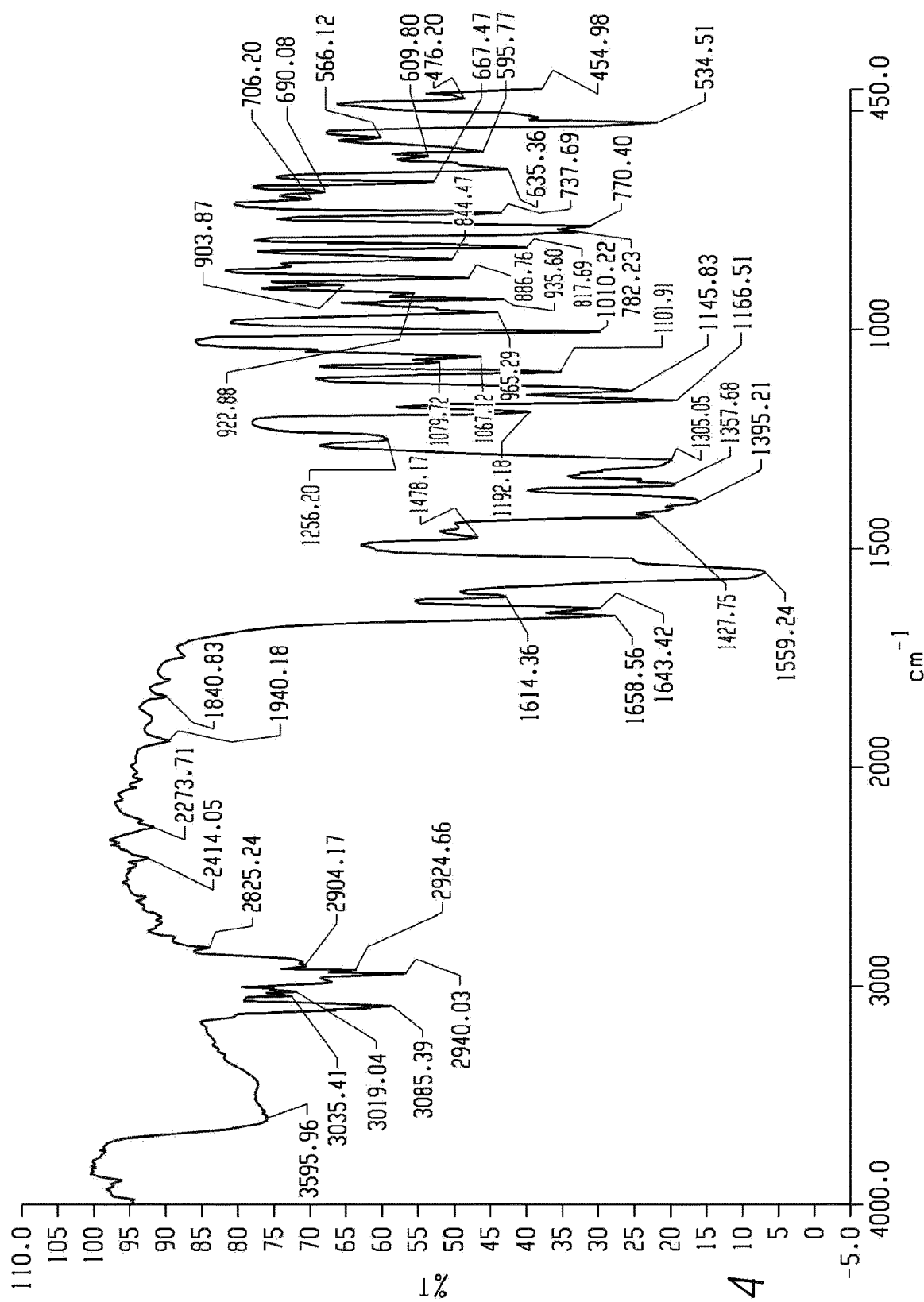
FIG. 4 shows a typical FT-IR spectrum of mesotrione copper chelate form II according to the present invention.

During the study on the polymorphic forms of mesotrione copper chelate, another polymorphic form referred to as form II was found. Unlike mesotrione copper chelate form I, copper chelate form II was found to be suitable for making, particularly solid formulations. Mesotrione copper chelate form II of the present invention can be identified by X-ray powder diffractometric pattern.

In one embodiment there is provided mesotrione copper chelate form II which exhibits an X-ray diffraction pattern expressed in 2θ(±0.2°), showing at least 3 of the following reflexes: 7.6, 9.1, 10.7, 11.8, 13.7, 15.4, 18.8, 21.0, 22.3, 23.8, 27.7, 28.7 and 29.5.

In another embodiment there is provided mesotrione copper chelate form II which exhibits an X-ray diffraction pattern expressed in 2θ(±0.2°), showing all of the following reflexes: 7.6, 9.1, 10.7, 11.8, 13.7, 15.4, 18.8, 21.0, 22.3, 23.8, 27.7, 28.7 and 29.5.

In one embodiment, there is provided mesotrione copper chelate form II characterized by the following reflexes expressed as 2θ values and interplanar spacings d as given in the below table:

| Angle (2θ ± 0.2°) | Interplanar spacings (d) Å |
|---|---|
| 7.6 | 11.5 |
| 9.1 | 9.6 |
| 10.7 | 8.3 |
| 11.8 | 7.4 |
| 13.7 | 6.4 |
| 15.4 | 5.8 |
| 18.8 | 4.8 |
| 21.0 | 4.2 |
| 22.3 | 4.0 |
| 23.8 | 3.7 |
| 27.7 | 3.2 |
| 28.7 | 3.1 |
| 29.5 | 3.0 |

In an embodiment of the present invention, there is provided a process for preparing mesotrione metal chelate polymorph.

In one embodiment, there is provided a process for preparing mesotrione metal chelate polymorph, said process comprising the following steps:
a) preparing a dispersion of mesotrione using a suitable base and water;
b) precipitating mesotrione metal chelate polymorph by addition of metal salt solution; and
c) filtration and isolation of mesotrione metal chelate polymorph.

In an embodiment of the present invention, the base of step (a) is selected from alkali or alkaline earth metal hydroxides, carbonates, bicarbonates or an ammonium base.

In another embodiment the base of step (a) is selected from sodium hydroxide or ammonium hydroxide.

In another embodiment the metal ions which are useful in forming the metal chelate polymorphs of the present invention include transition metal ions such as $Mn^{+2}$, $Co^{+2}$, $Cu^{+2}$, $Zn^{+2}$, $Fe^{+2}$, $Ni^{+2}$ and $Fe^{+3}$.

In another embodiment, the metal salts which are suitable for forming the metal chelate polymorphs of the present invention include metal salts of Mn, Co, Cu, Zn, Fe, Ni and Fe.

In yet another embodiment the metal ions of particular interest is selected from $Zn^{+2}$, $Fe^{+2}$ and $Cu^{+2}$.

In another embodiment, there is provided a process for preparing mesotrione copper chelate form I said process comprising the following steps:
a) preparing a dispersion of mesotrione using sodium hydroxide and water;
b) precipitating mesotrione metal chelate form I by addition of copper salt solution; and
c) filtration and isolation of mesotrione copper chelate form I.

In an embodiment, the pH of dispersion of step (a) varies from about 6 to about 10.

In an embodiment, in step (b) suitable copper salt is selected from chlorides, sulfates, nitrates, carbonates and phosphates.

Mesotrione copper chelate form I is advantageous especially for making liquid formulations. Particularly, mesotrione copper chelate form I was found to be useful in terms of ease of making formulation, handling the formulation especially during storage for longer duration. It has further been observed that formulations comprising mesotrione copper chelate form I are advantageous during dilution and application of the formulation. The physical characteristics such as bulk density and particle size demonstrate said advantages.

Mesotrione copper chelate form I exhibits characteristic bulk density. The bulk density of mesotrione copper chelate form I is from about 0.51 to about 0.535 gm/ml.

Mesotrione copper chelate form I possesses characteristic particle size. The median diameter or the medium value of the particle size distribution (D50 and D90) recorded for mesotrione copper chelate form I is given in the below table. The samples (a) and (b) are prepared as per process given in example 1.

| Sr. No. | Sample Name | Particle size (µm) | |
|---|---|---|---|
| | | D (0.5) | D (0.9) |
| 1 | Mesotrione copper chelate form I-a | 7.94 | 13.02 |
| 2 | Mesotrione copper chelate form I-b | 7.62 | 13.22 |

The above listed characteristic physical properties of mesotrione copper chelate form I demonstrates the advantages of making and using herbicidal formulations comprising mesotrione copper chelate form I. It has been observed by the inventors that due to smaller particle size, mesotrione copper chelate form I is suitable for preparing liquid formulation wherein repetitive and tedious milling is avoided to obtain required particle size. Moreover it has been surprisingly observed that while preparing solid formulations comprising mesotrione copper chelate form I, the strenuous milling process could be avoided completely. Further it has been observed that by avoiding the multiple milling processes, the possibility of morphological changes of mesotrione chelate are less leading to a physically and chemically stable formulation.

According to the present invention, there is provided a process for preparing mesotrione copper chelate form II.

In one embodiment, there is provided a process for preparing mesotrione copper chelate form II said process comprising the following steps:
a) preparing a dispersion of mesotrione using ammonium hydroxide and water;
b) precipitating mesotrione copper chelate form II by addition of copper salt solution; and
c) filtration and isolation of mesotrione copper chelate form II.

In an embodiment, the pH of dispersion of step (a) is from about 6 to about 9.

In an embodiment, in step (b) suitable copper salt is selected from chlorides, sulfates, nitrates, carbonates and phosphates.

Mesotrione copper chelate form II exhibits characteristic bulk density. The bulk density of mesotrione copper chelate form II is from about 0.61 to about 0.65 gm/ml.

Mesotrione copper chelate form II possesses characteristic particle size. The median diameter or the medium value of the particle size distribution (D50 and D90) recorded for mesotrione copper chelate form II is given in the below table. The samples (a) and (b) are prepared as per process given in example 2.

| Sr. No. | Sample Name | Particle size (µm) | |
|---|---|---|---|
| | | D (0.5) | D (0.9) |
| 1 | Mesotrione copper chelate form II-a | 17.58 | 34.08 |
| 2 | Mesotrione copper chelate form II-b | 16.74 | 27.33 |

It can be concluded from the above data that mesotrione copper chelate form II is suitable for making especially solid formulations wherein any milling process may not be required. Further, the inventors observed that the use of innovative copper chelate form II in formulations helps in preventing any undesired changes in crystal nature of mesotrione, resulting in stable formulations.

The invention further relates to formulations comprising mesotrione metal chelate polymorphs.

In an embodiment, there is provided formulations comprising mesotrione copper chelate form I or mesotrione copper chelate form II.

In an embodiment there is provided herbicidal formulations comprising mesotrione copper chelate form I.

In another embodiment, there is provided herbicidal formulations comprising mesotrione copper chelate form I and additives useful for the formulation of plant protection agents.

The present invention further provides a process for preparing herbicidal formulations comprising mesotrione copper chelate polymorphs.

In an embodiment, the present invention provides a process for preparing herbicidal formulation comprising mesotrione copper chelate polymorph, said process comprising the steps of:
a) preparing a dispersion of mesotrione using a suitable base and water;
b) adding metal salt solution to form mesotrione metal chelate polymorph
c) adding other agrochemical excipients if necessary;
d) optionally adding one or more other active ingredients; and
e) homogenizing the mixture.

In another embodiment there is provided a process for preparing an herbicidal formulation comprising mesotrione copper chelate polymorph, said process comprising the following steps:
a) preparing a dispersion of mesotrione using a suitable base and water;
b) adding copper salt solution to form mesotrione copper chelate form I;
c) adding other agrochemical excipients if necessary;
d) optionally adding one or more other active ingredients; and
e) homogenizing the mixture.

In yet another embodiment there is provided a process for preparing an herbicidal formulation comprising mesotrione copper chelate form I, said process comprising the following steps:
a) preparing a dispersion of mesotrione using sodium hydroxide and water;
b) precipitating mesotrione copper chelate form I by addition of copper salt solution;
c) filtering mesotrione copper chelate form I if necessary;
d) adding other agrochemical excipients if necessary;
e) optionally adding one or more other active ingredients; and
f) homogenizing the mixture.

In another embodiment there is provided a process for preparing an herbicidal formulation comprising mesotrione copper chelate form I, said process comprising the following steps:
a) preparing a dispersion of mesotrione using sodium hydroxide and water;
b) precipitating mesotrione copper chelate form I by addition of copper salt solution;
c) adding other agrochemical excipients if necessary;
d) optionally adding one or more other active ingredients; and
e) homogenizing the mixture.

In yet another embodiment there is provided a process for preparing an herbicidal formulation comprising mesotrione metal chelate form II, said process comprising the following steps:
a) preparing a dispersion of mesotrione using ammonium hydroxide and water;
b) adding metal salt solution to form mesotrione metal chelate form II;
c) adding other agrochemical excipients if necessary;
d) optionally adding one or more other active ingredients; and
e) homogenizing the mixture.

In yet another embodiment there is provided a process for preparing an herbicidal formulation comprising mesotrione copper chelate form II, said process comprising the following steps:
a) preparing a dispersion of mesotrione using ammonium hydroxide and water;
b) adding copper salt solution to form mesotrione metal chelate form II;
c) adding other agrochemical excipients if necessary;
d) optionally adding one or more other active ingredients; and
e) homogenizing the mixture.

In yet another embodiment there is provided a process for preparing an herbicidal formulation comprising mesotrione copper chelate form II, said process comprising the following steps:
a) preparing a dispersion of mesotrione using ammonium hydroxide and water;
b) precipitating mesotrione copper chelate form II by addition of copper salt solution; and
c) filtering mesotrione copper chelate form II if necessary;
d) adding other agrochemical excipients if necessary;
e) optionally adding one or more other active ingredients; and
f) homogenizing the mixture.

Mesotrione copper chelate form I of the invention is of particular interest in formulations of mesotrione in combination with one or more other plant protection agents.

In an embodiment, the mesotrione copper chelate form I of the invention is of particular interest in formulations of mesotrione in combination with one or more other plant protection agents wherein the concentration of mesotrione varies from about 0.01% to about 30% by weight of the composition.

In one embodiment, the present invention provides herbicidal formulations comprising mesotrione copper chelate form I and a second active ingredient along with suitable additives.

In another embodiment, the present invention provides herbicidal combinations comprising mesotrione copper chelate form I and a second active ingredient.

The second active ingredient is preferably a herbicide.

In an embodiment, the second herbicide that can be combined with mesotrione copper chelate form I of the invention is selected from but not limited to isoxazolidinone herbicides, urea herbicides, triazine herbicides, hydroxybenzonitrile herbicides, organophosphorus herbicides, thiocarbamate herbicides, pyridazine herbicides, chloroacetanilide herbicides; benzothiazole herbicides; carbanilate herbicides, cyclohexene oxime herbicides; picolinic acid herbicides; pyridine herbicides; quinolinecarboxylic acid herbicides; chlorotriazine herbicides, aryloxyphenoxypropionic herbicides, oxadiazolone herbicides; phenylurea herbicides, sulfonanilide herbicides; triazolopyrimidine herbicides, amide herbicides, pyridazine herbicides, dinitroaniline herbicides or combinations thereof.

In a preferred embodiment, the second herbicide is selected from a triazine herbicide. With respect to the present invention, the term triazine refers to chemical compounds from the group of their equivalents, metabolites, salts, esters, isomers and derivatives. Examples of triazine herbicides include chlorazine, cyanazine, cyprazine, eglinazine, ipazine, mesoprazine, procyazine, proglinazine, propazine, sebuthylazine, simazine, terbuthylazine, trietazine, dipropetryn, fucaojing and trihydroxytriazine.

Accordingly, there is provided a herbicidal formulation comprising mesotrione copper chelate form I and a triazine herbicide along with other suitable excipients. The composition comprises from about 0.01% to 30% by weight of mesotrione copper chelate form I and from about 1% to about 70% by weight of triazine herbicide.

In another embodiment, the herbicide that can be present along with the mesotrione copper chelate form I of the present invention is selected from organophosphorus herbicide. With respect to the present invention, the term organophosphorus refers to chemical compounds from the group of organophosphorus, their equivalents, metabolites, salts, esters, isomers and derivatives. Examples of organophosphorus herbicides include amiprofos-methyl, amiprofos, anilophos, bensulide, bilanafos, EBEP, fosamine, butamifos, clacyfos, 2,4-DEP, DMPA, glufosinate, glufosinate-P, glyphosate, piperophos, huangcaoling and shuangjiaancaolin.

In another preferred embodiment, the second herbicide is selected from chloroacetanilide herbicide. With respect to the present invention, the term "chloroacetanilide" refers to chemical compounds from the group of chloroacetanilide, their equivalents, metabolites, salts, esters, isomers and derivatives. Examples of chloroacetanilide herbicides include acetochlor, alachlor, butachlor, butenachlor, delachlor, diethatyl, dimethachlor, ethachlor, ethaprochlor, metazachlor, metolachlor, S-metolachlor, pretilachlor, propachlor, propisochlor, prynachlor, terbuchlor, thenylchlor, xylachlor.

More particularly the second herbicide is S-Metolachlor.

Accordingly, there is provided a herbicidal formulation comprising mesotrione copper chelate form I and chloroacetanilide herbicide along with other suitable excipients. The composition comprises from about 0.01% to 20% by weight of mesotrione copper chelate form I and from about 1% to about 70% by weight of chloroacetanilide herbicide.

In another embodiment according to the present invention there is provided a formulation comprising mesotrione copper chelate form I, chloroacetanilide herbicide and a triazine herbicide along with other suitable excipients. The composition comprises from about 0.01% to 20% by weight of mesotrione copper chelate form I, from about 1% to about 70% by weight of chloroacetanilide herbicide and from about 1% to about 70% by weight of triazine herbicide.

In another embodiment the present invention provides a composition comprising mesotrione copper chelate form I and S-metolachlor.

The inventors of the present invention observed that the composition comprising mesotrione copper chelate form I and S-metolachlor lead to low eye irritancy.

The formulations comprising mesotrione copper chelate form I of the present invention includes both solid and liquid based formulations such as powders, granules, dry formulations, solutions, emulsions, suspo-emulsions, suspensions and microencapsulations in polymeric substances.

Preferably, mesotrione copper chelate form I is suitable for liquid based formulations.

In an embodiment of the present invention, the formulations of mesotrione copper chelate form I further comprises a safener.

In an embodiment, the safener selected from the group consisting of quinoline derivatives; benoxacor; dichlormid; fenchlorazole ethyl; fenclorim; flurazole; fluxofenim; furilazole; isoxadifen ethyl; mefenpyr; mefenpyr diethyl, oxabetrinil, cyometrinil, dymron, dimepiperate, cloquintocet-mexyl and cypro-sulfamide.

In an embodiment there is provided herbicidal formulation comprising mesotrione copper chelate form II.

In another embodiment, there is provided herbicidal formulation comprising mesotrione copper chelate form II and additives useful for the formulation of plant protection agents.

Mesotrione copper chelate form II of the invention is of particular interest in formulations of mesotrione in combination with one or more other plant protection agents.

In an embodiment, the mesotrione copper chelate form II of the invention is of particular interest in formulations of mesotrione in combination with one or more other plant protection agents wherein the concentration of mesotrione varies from about 0.01% to about 30% by weight of the composition.

In a preferred embodiment, there is provided a herbicidal formulation comprising mesotrione copper chelate form II and a triazine herbicide along with other suitable excipients. The composition comprises from about 0.01% to 30% by weight of mesotrione copper chelate form II and from about 1% to about 70% by weight of triazine herbicide.

The formulations of the present invention further comprises customary adjuvants suitable for agrochemical formulation selected from solvents/carriers, surfactants, emulsifiers, dispersing agents, anti-foaming agents, anti-freezing agents, colorants, wetting agents, anticaking agents, structuring agents, biocides, viscosity modifiers and binding agents. The composition content of these adjuvants is not particularly limiting and may be determined by a skilled technician in the art according to the conventional protocols.

The present invention additionally relates to a method of controlling undesired weed species said method comprising applying an effective amount of a composition comprising mesotrione chelate polymorph to weeds or to their locus.

In an embodiment, there is provided a method of controlling undesired weed species, said method comprising applying an effective amount of a composition comprising mesotrione copper chelate form I or form II to weeds or to their locus.

In another embodiment, there is provided a method of controlling undesired weed species, said method comprising applying an effective amount of composition comprising mesotrione copper chelate form I or form II along with one or more other active ingredients to weeds or to their locus.

The formulations of the present invention may be sold as a pre-mix composition or a kit of parts such that individual components of the formulations may be mixed before spraying.

Therefore, in an aspect, the present invention provides a kit comprising mesotrione and a component comprising a suitable base and water.

In an embodiment, the components of the kit are instructed to be mixed before being used.

Thus, in this embodiment, the kit of the invention also comprises an instruction manual.

In another embodiment, the kit comprises mesotrione and component comprising a suitable base and water and a third component comprising at least one co-pesticide.

Inventors of the present invention succeeded in producing innovative polymorphs as well as using them in producing advantageous stable herbicidal formulations. The following specific examples illustrates the invention further.

EXAMPLES

Example 1: Process for Preparing Mesotrione Copper Chelate Form I

A slurry of mesotrione was prepared by adding 522 g of mesotrione into 2 lts of water. The pH of the slurry was raised to the range of 7-10 with 20% sodium hydroxide solution. The mixture was stirred for one hour followed by the addition of 30% copper sulfate solution. The reaction mixture was stirred for 2-3 hours and the pH of the mixture was observed in the range of 4.8-5.2. The resulting slurry of mesotrione copper chelate form I was filtered, washed with hot water and dried under vacuum (555 gm). A sample was analyzed by p-XRD and the spectra obtained is presented in FIG. 1.

Example 2: Process for Preparing Mesotrione Copper Chelate Form II

A slurry of mesotrione was prepared by adding 345 g of mesotrione into 1.4 lts of water. The pH of the slurry was raised to the range of 6-9 with ammonia solution. The mixture was stirred for one hour followed by the addition of 20% copper sulfate solution. The reaction mixture was stirred for 2-3 hours and the pH of the mixture was observed in the range of 4.5-5.5. The resulting slurry of mesotrione copper chelate form II was filtered, washed with hot water and dried under vacuum (372 gm). A sample was analyzed by p-XRD and the spectra obtained is presented in FIG. 111.

Example 3: A Suspo-Emulsion Formulation of Mesotrione and S-Metolachlor According to the Present Invention has been Prepared as Follows a) Preparation Mesotrione (35)% suspension concentrate (SC)

| Ingredients | % (w/w) |
|---|---|
| Mesotrione copper chelate form I | 35 |
| propylene glycol | 6.0 |
| DM water (QS) | 59.0 |
| Total | 100 |

Procedure: Mesotrione copper chelate form I was mixed with the listed ingredients and the mixture was homogenized by stirring and subjected to wet grinding to achieve required particle size.

b) Preparation of S-Metolachlor (65)% oil-in-water emulsion(EW)

| Ingredients | % (w/w) |
|---|---|
| S-metolachlor | 66.67 |
| EO PO block copolymer | 2.65 |
| DM water (QS) | 30.68 |
| Total | 100 |

Procedure: S-metolachlor was mixed with the listed ingredients and homogenized by stirring well to form the oil-in-water emulsion.

c) Preparation of Mesotrione+S-Metolachlor suspoemulsion formulation(SE)

| Ingredients | % (w/w) |
|---|---|
| S-metolachlor 65 EW | 58.5 |
| Mesotrione copper chelate form I 35 SC | 10.86 |
| Benoxacor | 2.0 |
| EO PO block copolymer | 8.0 |
| Propylene glycol | 3.0 |
| DM water (QS) | 15.59 |
| Total | 100 |

Procedure: S-metolachlor EW was mixed with benoxacor, EO PO block copolymer and water. Mesotrione chelate form I SC was then added and stirred. The mixture was further homogenized by stirring until it was uniform. The formulation was found to be stable and no sedimentation or thickening observed during storage.

Example 4: A Suspo-Emulsion Formulation of Mesotrione, S-Metolachlor and Atrazine According to the Present Invention has been Prepared as Follows a) Preparation of Mesotrione (35)% suspension concentrate(SC):

| Ingredients | % (w/w) |
|---|---|
| Mesotrione copper chelate form I | 35.0 |
| EO PO block copolymer | 6.0 |
| DM water (QS) | 59.0 |
| Total | 100 |

Procedure: Mesotrione copper chelate form I was mixed with the listed ingredients and the mixture was homogenized by stirring.

b) Preparation of s-metolachlor (65)% oil-in-water emulsion(EW)

| Ingredients | % (w/w) |
|---|---|
| S-metolachlor | 66.67 |
| EO PO block copolymer | 2.65 |
| DM water (QS) | 30.68 |
| Total | 100 |

Procedure: S-metolachlor was mixed with the listed ingredients and homogenized by stirring to form the oil-in-water emulsion.

c) Preparation of atrazine (58)% suspension concentrate (SC):

| Ingredients | % (w/w) |
|---|---|
| Atrazine | 58.0 |
| EO PO block copolymer | 5.0 |
| DM water (QS) | 37.0 |
| Total | 100 |

Procedure: Atrazine was mixed with with the listed ingredients homogenized by stirring to prepare a homogenous suspension.

d) Preparation of S-metolachlor, mesotrione and atrazine suspo-emulsion formulation(SE)

| Ingredients | % (w/w) |
|---|---|
| S-metolachlor 65 EW | 45.23 |
| Mesotrione copper chelate form I 35 SC | 8.40 |
| Atrazine 58% SC | 18.97 |
| Benoxacor | 2.0 |
| EO PO block copolymer | 9.0 |
| Propylene glycol | 3.0 |
| DM water (QS) | 13.40 |
| Total | 100 |

Procedure: S-metolachlor EW was mixed with water, benoxacor, EO PO block copolymer and propylene glycol followed by the addition of mesotrione copper chelate form I SC and atrazine SC. Water was added and homogenized by stirring until getting a uniform suspension. The formulation was found to be stable and no sedimentation or precipitation observed during storage.

Example 5: A Suspo-Emulsion Formulation of Mesotrione and S-Metolachlor According to the Present Invention has been Prepared as Follows a) Preparation Mesotrione (35)% suspension concentrate (SC)

| Ingredients | % (w/w) |
|---|---|
| Mesotrione | 35.0 |
| Copper sulphate | 13.00 |
| Sodium hydroxide (20% lye) | 20.00 |
| EO PO block copolymer | 6.00 |
| DM water (QS) | 26.00 |
| Total | 100 |

Procedure: Mesotrione was mixed with the listed ingredients and the mixture was homogenized by stirring to form mesotrione copper chelate form I SC which is further subjected to wet grinding to achieve required particle size.

b) Preparation of S-Metolachlor (65)% oil-in-water emulsion(EW)

| Ingredients | % (w/w) |
|---|---|
| S-metolachlor | 66.67 |
| EO PO block copolymer | 2.65 |
| DM water (QS) | 30.68 |
| Total | 100 |

Procedure: S-metolachlor was mixed with the listed ingredients and homogenized by stirring to form the oil-in-water emulsion.

c) Preparation of Mesotrione+S-Metolachlor suspoemulsion formulation(SE)

| Ingredients | % (w/w) |
|---|---|
| S-metolachlor 65 EW | 58.5 |
| Mesotrione copper chelate form I 35 SC | 10.86 |
| Benoxacor | 2.0 |
| EO PO block copolymer | 10.0 |
| Propylene glycol | 3.0 |
| DM water (QS) | 15.64 |
| Total | 100 |

Procedure: S-metolachlor EW was mixed with benoxacor, EO PO block copolymer, propylene glycol and water. Mesotrione copper chelate form I SC was then added and stirred. The mixture was further homogenized by stirring until it was uniform. The formulation was found to be stable and no sedimentation or thickening observed during storage.

Acute Eye Irritation Study

A composition comprising mesotrione copper chelate form I and S-metolchlor prepared according to the present invention (example 3) was tested for eye irritation. This study was performed to assess the acute eye irritation effect of the formulation.

Study Guidelines

The present study was conducted according to: EPA, 1998: The United States Environmental Protection Agency (EPA), Health Effects Test Guidelines, OCSPP 870.2400, Acute Eye Irritation (EPA 712-C-98-195) (August 1998).

OECD, 2012: The Organization for Economic Co-operation and Development (OECD) Guidelines for the Testing of Chemicals, OECD 405, Acute Eye Irritation/Corrosion, adopted by the Council on Oct. 2, 2012.

In an acute eye irritation study, three adult female New Zealand White rabbits were given a single ocular application of 0.1 mL of formulation prepared according to example 3 of the present invention on right eye of the rabbit while the contralateral eye remained untreated and served as the control. Initially one rabbit was tested. Based on the results obtained at 24 h post Test Item Application (TIA), the irritation response was confirmed by testing two additional rabbits simultaneously. Observations were made at 1, 24, 48 and 72 h post-TIA. General health status was also checked.

Individual Scores of Eye Reactions Post-Application

| | Control Eye Sex: Female | | | | | | | | | | | |
|---|---|---|---|---|---|---|---|---|---|---|---|---|
| | Rabbit Number | | | | | | | | | | | |
| | 1 | | | | 2 | | | | 3 | | | |
| | Site of Application | | | | | | | | | | | |
| | Left Hour | | | | Left Hour | | | | Left Hour | | | |
| Reaction | 1 | 24 | 48 | 72 | 1 | 24 | 48 | 72 | 1 | 24 | 48 | 72 |
| Opacity: degree of density | 0 | 0 | 0 | 0 | 0 | 0 | 0 | 0 | 0 | 0 | 0 | 0 |

-continued

Control Eye
Sex: Female

| | Rabbit Number | | | | | | | | | | | |
|---|---|---|---|---|---|---|---|---|---|---|---|---|
| | 1 | | | | 2 | | | | 3 | | | |
| | Site of Application | | | | | | | | | | | |
| | Left | | | | Left | | | | Left | | | |
| | Hour | | | | Hour | | | | Hour | | | |
| Reaction | 1 | 24 | 48 | 72 | 1 | 24 | 48 | 72 | 1 | 24 | 48 | 72 |
| Iris | 0 | 0 | 0 | 0 | 0 | 0 | 0 | 0 | 0 | 0 | 0 | 0 |
| Conjunctivae (Redness) | 0 | 0 | 0 | 0 | 0 | 0 | 0 | 0 | 0 | 0 | 0 | 0 |
| Conjunctivae (Chemosis) | 0 | 0 | 0 | 0 | 0 | 0 | 0 | 0 | 0 | 0 | 0 | 0 |

Treated eye

| | Rabbit Number | | | | | | | | | | | |
|---|---|---|---|---|---|---|---|---|---|---|---|---|
| | 1 | | | | 2 | | | | 3 | | | |
| | Site of Application | | | | | | | | | | | |
| | Right | | | | Right | | | | Right | | | |
| | Hour | | | | Hour | | | | Hour | | | |
| Reaction | 1 | 24 | 48 | 72 | 1 | 24 | 48 | 72 | 1 | 24 | 48 | 72 |
| Opacity: degree of density | 0 | 0 | 0 | 0 | 0 | 0 | 0 | 0 | 0 | 0 | 0 | 0 |
| Iris | 0 | 0 | 0 | 0 | 0 | 0 | 0 | 0 | 0 | 0 | 0 | 0 |
| Conjunctivae (Redness) | 1 | 2 | 1 | 0 | 1 | 1 | 0 | 0 | 1 | 1 | 0 | 0 |
| Conjunctivae (Chemosis) | 1 | 1 | 0 | 0 | 1 | 0 | 0 | 0 | 1 | 0 | 0 | 0 |

Individual Corneal Observations 24 h Post Application Using Fluorescein Dye Staining Control Eye
Sex: Female

| Rabbit Number | Control Eye | Day | Fluorescein Staining Response | Details of Corneal Observation in Control Eye |
|---|---|---|---|---|
| 1 | left | 1 | Negative | No damage to corneal epithelium was observed |
| | | 2 | Negative | No damage to corneal epithelium was observed |
| | | 3 | Negative | No damage to corneal epithelium was observed |
| 2 | left | 1 | Negative | No damage to corneal epithelium was observed |
| | | 2 | Negative | No damage to corneal epithelium was observed |
| 3 | left | 1 | Negative | No damage to corneal epithelium was observed |
| | | 2 | Negative | No damage to corneal epithelium was observed |

| Rabbit N° | Control Eye | Day | Fluorescein Staining Response | Details of Corneal Observation in Control Eye |
|---|---|---|---|---|
| | | | Treated Eye | |
| 1 | Right | 1 | Positive | 25% damage to corneal epithelium was observed |
| | | 2 | Positive | 10% damage to corneal epithelium was observed |
| | | 3 | Negative | No damage to corneal epithelium was observed |
| 2 | Right | 1 | Positive | 10% damage to corneal epithelium was observed |
| | | 2 | Negative | No damage to corneal epithelium was observed |
| 3 | Right | 1 | Positive | 10% damage to corneal epithelium was observed |
| | | 2 | Negative | No damage to corneal epithelium was observed |

Based on the results of this study, an indication of the classifications for the tested formulation is as follows:

Globally Harmonized System of Classification and Labelling of Chemicals (GHS 2015): Not classified as an eye irritant EPA Toxicity Categories (December 2002):
Category III The instant invention is more specifically explained by examples given above. However, it should be understood that the scope of the present invention is not limited by the examples in any manner. It will be appreciated by any person skilled in this art that the present invention includes the given examples and further can be modified and altered without departing from the novel teachings and advantages of the invention which are intended to be included within the scope of the invention.

The invention claimed is:

1. Mesotrione copper chelate form II which exhibits an X-ray diffraction pattern expressed in $2\theta(\pm 0.2°)$, showing at least 3 of the following reflexes: 7.6, 9.1, 10.7, 11.8, 13.7, 15.4, 18.8, 21.0, 22.3, 23.8, 27.7, 28.7 and 29.5.

2. A process for preparing the mesotrione copper chelate form II of claim 1, said process comprising:
   a. preparing a dispersion of mesotrione in ammonium hydroxide and water; and
   b. precipitating mesotrione copper chelate form II from the dispersion by adding a copper salt solution.

3. An herbicidal composition comprising the mesotrione copper chelate form II of claim 1 and at least one agrochemical excipient.

4. The herbicidal composition of claim 3, further comprising at least another agrochemical ingredient.

5. The herbicidal composition of claim 4, wherein said agrochemical ingredient is an herbicide.

6. The herbicidal composition of claim 5, wherein said herbicide is selected from the group consisting of isoxazolidinone herbicides, urea herbicides, triazine herbicides, hydroxybenzonitrile herbicides, organophosphorus herbicides, thiocarbamate herbicides, pyridazine herbicides, chloroacetanilide herbicides; benzothiazole herbicides; carbanilate herbicides, cyclohexene oxime herbicides; picolinic acid herbicides; pyridine herbicides; quinolinecarboxylic acid herbicides; chlorotriazine herbicides, aryloxyphenoxypropionic herbicides, oxadiazolone herbicides; phenylurea herbicides, sulfonanilide herbicides; triazolopyrimidine herbicides, amide herbicides, pyridazine herbicides, dinitroaniline herbicides, ands combinations thereof.

7. The herbicidal composition of claim 5, wherein said herbicide is selected from a triazine herbicide and a chloroacetanilide herbicide.

8. A method of controlling undesired weed species, said method comprising applying an effective amount of a composition comprising the mesotrione copper chelate form II of claim 1 to the weeds or to their locus.

9. A kit comprising the mesotrione copper chelate form II of claim 1 in solid form and a component comprising a base and water.

10. The kit of claim 9, wherein said base is ammonium hydroxide.

11. The kit of 9, comprising an instruction manual including instructions to mix the components of the kit prior to being used.

12. The kit of 9, further comprising at least another agrochemical active ingredient component.

* * * * *